US00PP14693P29

(12) United States Plant Patent
Farrow

(10) Patent No.: US PP14,693 P2
(45) Date of Patent: Apr. 13, 2004

(54) NANDINA PLANT NAMED 'MONFAR'

(50) Latin Name: *Nandina domestica*
Varietal Denomination: Monfar

(75) Inventor: Michael W. Farrow, Earleville, MD (US)

(73) Assignee: Holly Hill Farms, Inc., Earleville, MD (US)

( * ) Notice: Subject to any disclaimer, the term of this patent is extended or adjusted under 35 U.S.C. 154(b) by 0 days.

(21) Appl. No.: 10/317,306

(22) Filed: Dec. 12, 2002

(51) Int. Cl.[7] ..... A01H 5/00
(52) U.S. Cl. ..... Plt./235
(58) Field of Search ..... Plt./235, 226

(56) References Cited

U.S. PATENT DOCUMENTS

PP5,656 P * 2/1986 Barr ..... Plt./235
PP5,659 P * 2/1986 Barr ..... Plt./235

OTHER PUBLICATIONS

UPOV ROM GTITM Computer Database, GTI JOUVE Retrieval Software 2003/04 citation for 'Monfar'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct Nandina plant named 'Monfar', characterized by its upright, mounded, dwarf and compact plant habit; developing leaves burgundy red in color; burgundy red coloration retained throughout the year; freely branching habit; and hardy to USDA Hardiness Zone 6B.

1 Drawing Sheet

Botanical classification/cultivar designation: *Nandina domestica* cultivar Monfar.

BACKGROUND OF THE INVENTION

The present invention relates to a new and distinct cultivar of Nandina, botanically known as *Nandina domestica,* and hereinafter referred to by the name 'Monfar'.

The new Nandina is a product of a cross-pollination during the spring of 1993 of two unidentified selections of *Nandina domestica,* not patented. The new Nandina was discovered and selected by the Inventor in a controlled environment in Earleville, Md. during the summer of 1996, as a single plant within the progeny resulting from the cross-pollination.

Asexual reproduction of the new Nandina by cuttings taken in a controlled environment in Earleville, Md., since June, 1996, has shown that the unique features of this new Nandina are stable and reproduced true to type in successive generations.

SUMMARY OF THE INVENTION

The cultivar Monfar has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Monfar'. These characteristics in combination distinguish 'Monfar' as a new and distinct cultivar of Nandina:

1. Upright, mounded, dwarf and compact plant habit.
2. Developing leaves burgundy red in color; burgundy red coloration retained throughout the year.
3. Freely branching habit.
4. Hardy to USDA Hardiness Zone 6B.

Compared to plants of the parent selections, plants of the new Nandina are much more dwarf and have shorter internodes. Plants of the new Nandina also differ from plants of the parent selections in leaf coloration. In addition, plants of the parent selections usually produce flowers and berries whereas plants of the new Nandina do not produce flowers and berries.

Plants of the new Nandina can be compared to plants of the Nandina cultivar Gulf Stream, disclosed in U.S. Plant Pat. No. 5,656. In side-by-side comparisons conducted in Earleville, Md., plants of the new Nandina differed from plants of the cultivar Gulf Stream primarily in developing foliage coloration as plants of the new Nandina produced burgundy red-colored leaves whereas plants of the cultivar Gulf Stream produced orange-colored leaves.

Plants of the new Nandina can also be compared to plants of the Nandina cultivar Moon Bay, disclosed in U.S. Plant Pat. No. 5,659. In side-by-side comparisons conducted in Earleville, Md., plants of the new Nandina differed from plants of the cultivar Moon Bay in developing foliage coloration as plants of the new Nandina produced burgundy red-colored leaves whereas plants of the cultivar Moon Bay produced light green-colored leaves. In addition, plants of the new Nandina were larger than plants of the cultivar Moon Bay.

BRIEF DESCRIPTION OF THE PHOTOGRAPHS

The accompanying colored photographs illustrate the overall appearance of the new Nandina, showing the colors as true as it is reasonably possible to obtain in colored reproductions of this type. Colors in the photographs may differ slightly from the color values cited in the detailed botanical description which accurately describe the colors of the new Nandina.

The photograph at the top of the sheet comprises a side perspective view of a typical plant of 'Monfar' grown in a container.

The photograph at the bottom left of the sheet is a close-up view of a typical lateral branch of 'Monfar'.

The photograph at the bottom right of the sheet is a close-up of typical developing and fully expanded leaves of 'Monfar'.

DETAILED BOTANICAL DESCRIPTION

The aforementioned photographs and following observations and measurements describe plants grown in Azusa, Calif., grown in five-gallon containers in an outdoor nursery during the spring and under conditions which closely approximate commercial production. During the production of the plants, day temperatures ranged from 55 to 105° F. and night temperatures ranged from 30 to 65° F. Plants were about 2.5 years old when the photographs and the description were taken. In the description color references are made to The Royal Horticultural Society Colour Chart, 1995 Edition, except where general terms of ordinary dictionary significance are used.

Botanical classification: *Nandina domestica* cultivar Monfar.

Parentage:

*Female, or seed, parent.*—Unidentified selection of *Nandina domestica,* not patented.

*Male, or pollen, parent.*—Unidentified selection of *Nandina domestica,* not patented.

Propagation:

*Type.*—By cuttings.

*Time to initiate roots.*—About 21 days.

*Root description.*—Fine, fibrous; whitish in color.

*Rooting habit.*—Dense; freely branching.

Plant description:

*Plant form and growth habit.*—Upright, mounded, dwarf and compact plant habit; appropriate for container production; perennial shrub. Low to moderately vigorous growth habit.

*Branching habit.*—Freely branching; usually about ten basal branches each with about six or seven lateral branches.

*Plant height.*—About 28 cm.

*Plant diameter* (*area of spread*).—About 42 cm.

*Lateral branch description.*—Length: About 25 cm. Diameter: About 4 to 6 mm. Internode length: About 3 to 10 cm. Aspect: Upright. Texture: Smooth. Color: Young stems: 146B. Woody stems: 199A.

*Foliage description.*—Arrangement: Alternate, triternately compound. Length: About 12 to 14 cm. Width: About 18 cm. Leaflet shape: Narrowly ovate. Leaflet apex: Acute. Leaflet base: Attenuate. Leaflet margin: Entire. Leaflet texture, upper and lower surfaces: Smooth, glabrous. Leaflet venation pattern: Pinnate. Color: Developing leaflets, upper surface: 59A. Developing leaflets, lower surface: 183B. Fully expanded leaflets, upper surface: 147A. Fully expanded leaflets, lower surface: 147B. Venation, upper surface: 147A. Venation, lower surface: 147C. Leaflet petiole: Length: About 3 cm. Diameter: About 2.25 mm. Texture, upper and lower surfaces: Smooth, glabrous. Color, upper and lower surfaces: 146A.

Flower description: Flower development has not been observed on plants of the new Nandina.

Disease/pest resistance: Plants of the new Nandina have not been observed to be resistant to pathogens and pests common to Nandina.

Hardiness: Plants of the new Nandina are hardy to USDA Zone 6B.

It is claimed:

1. A new and distinct Nandina plant named 'Monfar', as illustrated and described.

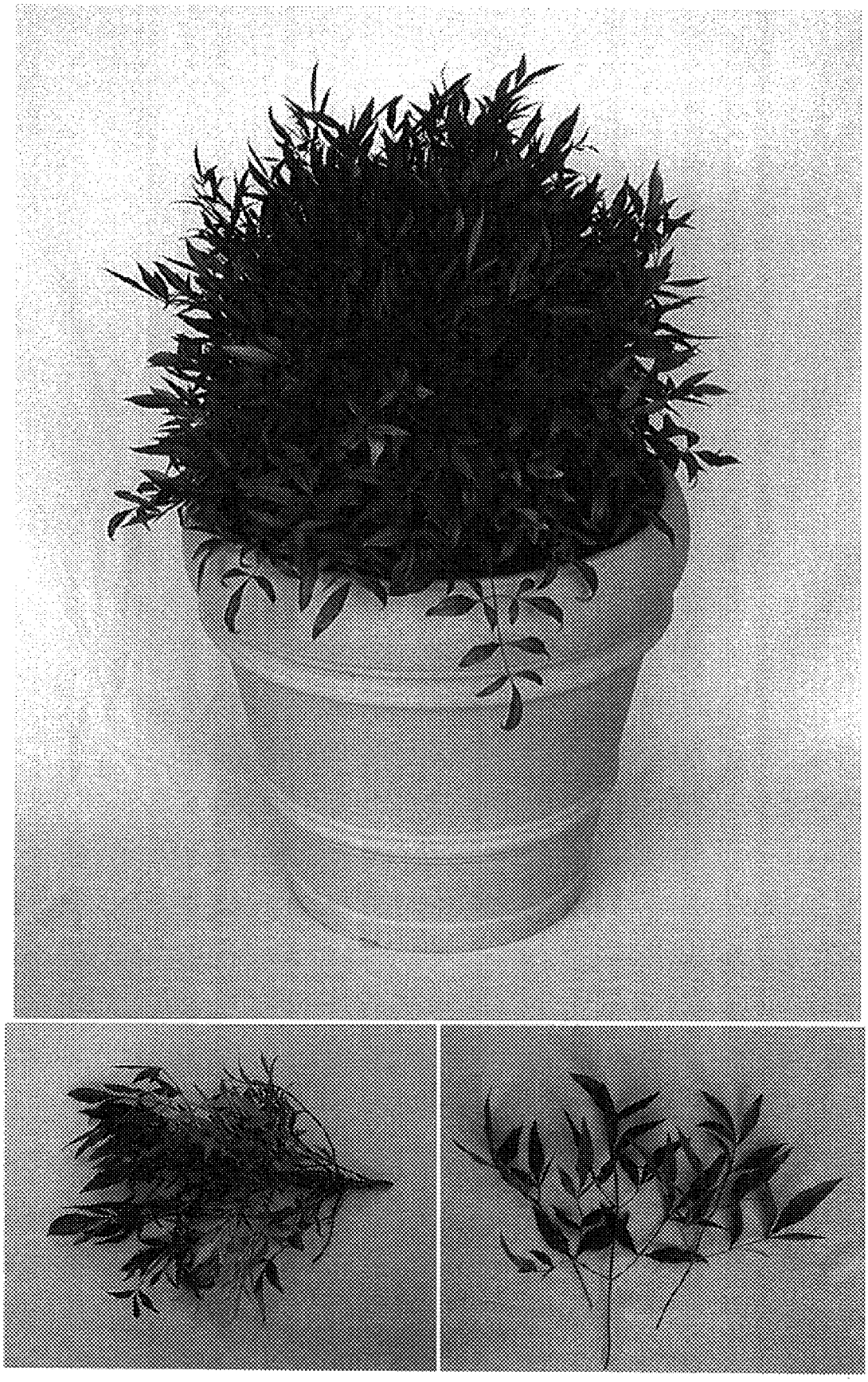

* * * * *